US011850367B2

(12) United States Patent
Nagai

(10) Patent No.: US 11,850,367 B2
(45) Date of Patent: Dec. 26, 2023

(54) DEVICE FOR MANAGING EPILEPSY

(71) Applicant: Yoko Nagai, East Sussex (GB)

(72) Inventor: Yoko Nagai, East Sussex (GB)

( * ) Notice: Subject to any disclaimer, the term of this patent is extended or adjusted under 35 U.S.C. 154(b) by 31 days.

(21) Appl. No.: 16/465,056

(22) PCT Filed: Nov. 28, 2017

(86) PCT No.: PCT/GB2017/000172
§ 371 (c)(1),
(2) Date: May 29, 2019

(87) PCT Pub. No.: WO2018/100330
PCT Pub. Date: Jun. 7, 2018

(65) Prior Publication Data
US 2019/0328998 A1 Oct. 31, 2019

(30) Foreign Application Priority Data
Nov. 30, 2016 (GB) ..................... 1620323

(51) Int. Cl.
*A61M 21/02* (2006.01)
*G16H 50/30* (2018.01)
(Continued)

(52) U.S. Cl.
CPC ........... *A61M 21/02* (2013.01); *A61B 5/4836* (2013.01); *G16H 50/20* (2018.01); *G16H 50/30* (2018.01);
(Continued)

(58) Field of Classification Search
CPC .......... A61M 21/02; A61M 2021/0022; A61M 2021/0027; A61M 2021/0044
See application file for complete search history.

(56) References Cited

U.S. PATENT DOCUMENTS 6,102,847 A    8/2000  Stielau
8,271,077 B1   9/2012  Rotenberg
(Continued)

FOREIGN PATENT DOCUMENTS

EP    2416698        9/2013
TW    201204322 A1   2/2012
(Continued)

OTHER PUBLICATIONS

PCT Notification of Transmittal of International Search Report and The Written Opinion of the International Searching Authority dated Jun. 4, 2018, issued from the International Searching Authority in related PCT Application No. PCT/GB2017/000172 (16 pages).
(Continued)

*Primary Examiner* — Carrie R Dorna
(74) *Attorney, Agent, or Firm* — MacMillan, Sobanski & Todd, LLC

(57) ABSTRACT

A treatment device configured noninvasively to treat neurological conditions and/or neuropsychiatric conditions, designed to modulate autonomic nervous system through biofeedback configured to change brain network. The treatment device comprising: physiological sensor, storage piling psychological data and operating controller to effectively
(Continued)

provide at least one of biofeedback and tactile stimulation to the individual to curtail neurological and/or neuropsychiatric events.

14 Claims, 3 Drawing Sheets

(51) Int. Cl.
  *A61M 21/00* (2006.01)
  *G16H 50/20* (2018.01)
  *A61B 5/00* (2006.01)
(52) U.S. Cl.
  CPC .............. *A61M 2021/0022* (2013.01); *A61M 2021/0027* (2013.01); *A61M 2021/0044* (2013.01); *A61M 2230/06* (2013.01); *A61M 2230/08* (2013.01); *A61M 2230/42* (2013.01); *A61M 2230/50* (2013.01); *A61M 2230/63* (2013.01); *A61M 2230/65* (2013.01)

(56) References Cited

U.S. PATENT DOCUMENTS

| | | | |
|---|---|---|---|
| 2003/0195588 A1 | 9/2003 | Fischell | |
| 2005/0197590 A1 | 9/2005 | Osorio et al. | |
| 2008/0077191 A1 | 3/2008 | Morrell | |
| 2008/0214903 A1 | 9/2008 | Orbach | |
| 2011/0245633 A1* | 10/2011 | Goldberg | A61B 5/165 |
| | | | 600/301 |
| 2015/0272494 A1 | 10/2015 | Fuerst | |
| 2016/0206236 A1 | 7/2016 | Dilorenzo et al. | |
| 2017/0340270 A1* | 11/2017 | Ganesh | A61H 23/02 |
| 2018/0088669 A1* | 3/2018 | Ramaprakash | A61B 5/6803 |
| 2020/0324104 A1* | 10/2020 | Labuschagne | A61N 1/0476 |

FOREIGN PATENT DOCUMENTS

| | | |
|---|---|---|
| WO | 2011109716 A2 | 9/2011 |
| WO | 2012071545 A1 | 5/2012 |

OTHER PUBLICATIONS

GB Search Report dated May 11, 2017, issued from the GB Intellectual Property Office in related GB Application No. GB1620323. 4. 4 pages.

Nagai et al., "Clinical Efficacy of galvanic skin response biofeeback training in reducing seizures in adult epilepsy: a preliminary randomized controlled study", Epilepsy & Behavior, 2004, vol. 5, pp. 216-223.

Fried et al., "Behavioral Control of Intractable Idiopathic Seizures: I. Self-Regulation of End-Tidal Carbon Dioxide", Psychosomatic Medicine, 1984, vol. 46, No. 4, pp. 315-331.

Rockstroh et al., "Cortical self-regulation in patients with epilepsies", Epilepsy Research, 1993, vol. 14, pp. 63-72.

Sterman et al., "Suppression of Seizures in an Epileptic Following Sensorimotor EEG Ffedback Training", Electroencephalography and Clinical Neurophysiology, 1972, vol. 33, pp. 89-95.

Japanese Notification of Reason for Refusal, Japanese Patent Application No. 2019-530005, dated Oct. 18, 2021.

Nagai, "Biofeedback treatment for epilepsy", Department of Clinical and Experimental Epilepsy, Institute of Neurology, University College London, pp. 1-8.

Japanese Notification of Reasons for Refusal, Japanese Patent Application No. 2019-530005, dated Jul. 26, 2022.

Bympathetic Nervous System (SNS), Cleveland Clinic, (undated)—11 pages.

* cited by examiner

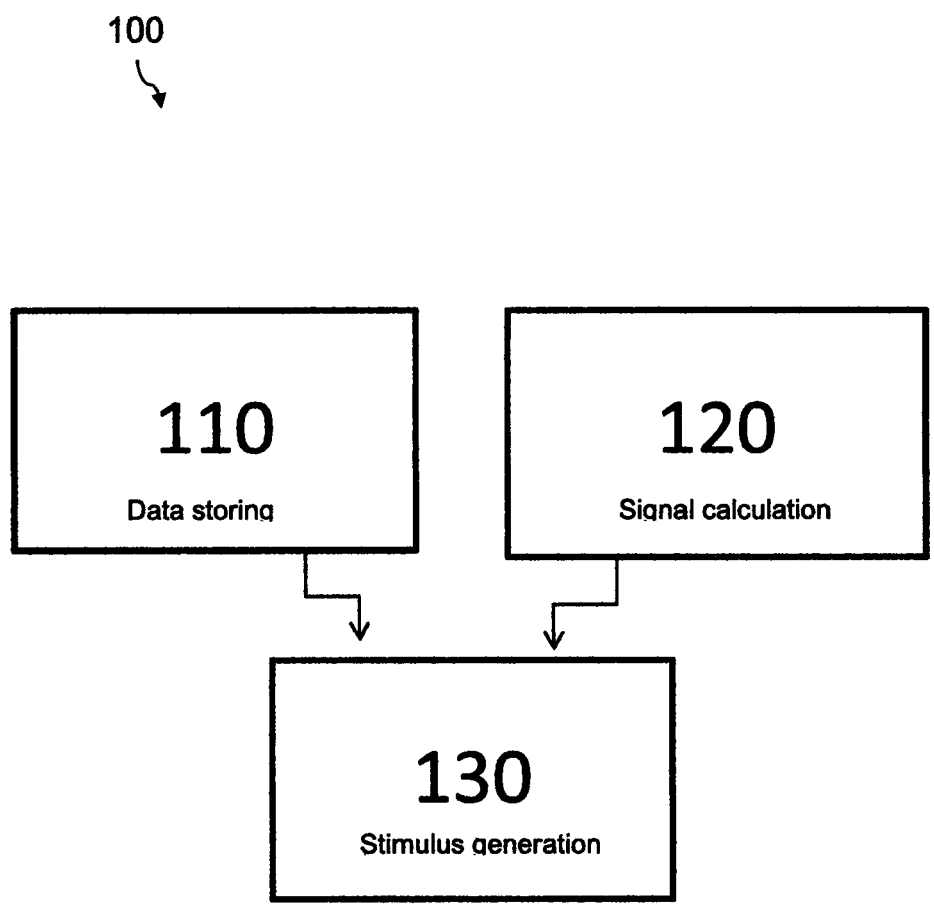

DEVICE FOR MANAGING EPILEPSY

This disclosure relates to a treatment device for neurological and/or neuropsychiatric conditions, and in particular, but not exclusively, relates to a device for the treatment of epilepsy, and/or other non-epileptic conditions.

BACKGROUND OF THE INVENTION

Epilepsy is a neurological disorder characterized by sensory disturbance, loss of consciousness, or convulsions, and is associated with abnormal electrical activity in the brain. The effects of epilepsy vary widely between sufferers, the only common feature being the occurrence of epileptic seizures. The frequency and severity of such occurrences also varies very widely, as does the ability of sufferers to control them, or indeed to predict an occurrence.

The potential dangers of such occurrences have led to very substantial efforts being made to find a cure, or if not a cure then palliative or alleviative measures, for treating epilepsy. As a result, there is a substantial body of research that has been carried out, which has led to an ability to treat epilepsy in many sufferers, though the effectiveness of such treatment can vary significantly.

A large range of synthetic therapeutic drugs is available which affect epilepsy sufferers in different ways. In a substantial proportion of cases, improvements in the management of epilepsy for an individual patient can be achieved, but this tends to be accompanied by considerable side effects and, accordingly, drug-based management of epilepsy is not seen as a universally positive form of treatment. Indeed, around 30% of all epilepsy sufferers have a resistance to the drugs known for such treatment.

For patients who do not respond to anti-epileptic drugs, further treatment options typically involve surgery, Vagus Nerve Stimulation (VNS) and Deep Brain Stimulation. There are also some surgically implantable devices that attempt to detect seizures before they develop, U.S. Pat. Nos. 7,813,793, 0,077,191 and 9,044,188. However, these devices are not yet successfully utilized to terminate seizures.

The occurrence of epileptic seizures, and their strength and frequency, correlate with mental, emotional and/or, physical states. Effective biofeedback device that monitors psychological and physiological state and that can curtail abnormal brain activity without unnecessary drug administration, invasive surgery or other implanted devices would be appreciated by the patients.

SUMMARY OF INVENTION

According to an aspect of the present disclosure there is provided a treatment device configured to treat neurological conditions and/or neuropsychiatric conditions, the treatment device comprising: a sensor configured to determine a physiological condition of an individual; a storage module configured to store data regarding the psychological state and behavioural information of the individual; and a controller operatively connected to the sensor and the storage module, the controller being configured to provide at least one of biofeedback and tactile stimulation to the individual to activate sympathetic nerve activity based on the physiological condition of the individual and the data regarding the psychological state and behavioural information of the individual. The present disclosure is advantageous because it provides a more accurate way to determine the risk of a neurological episode occurring with a combination of sensor function and stored data, which helps increase the quality of life of those individuals that suffer from neurological disorders, such as epilepsy. The treatment device may be configured to prevent and/or disperse one or more neurological events in a short period of time, for example within a matter of minutes or seconds preceding the onset of a neurological event, such as a seizure.

Biofeedback is a patient-guided treatment that teaches an individual to control physiological responses such as heart rate, muscle tension, pain, body temperature, brain waves, or other bodily functions and processes through bodily state change, visualization, or other cognitive control techniques.

Tactile stimulation is the deliberate elicitation of any of a range of sensations perceived thorough the sense of touch. The stimulation can be delivered by any means and to any part of the body where touch can be felt.

Thus, biofeedback and tactile stimulation are physiological modulation techniques that can be used to increase sympathetic activity, which reduces the cortical potential, which represent group of neuronal excitation. In other words, biofeedback and tactile stimulation can be used to alter the autonomic state of the individual to reduce cortical excitation and alter neural network, for example by sedating brain activity.

The storage module may be configured to store data regarding seizure events of the individual. The controller may be configured to provide biofeedback/tactile stimulation based on the data regarding the seizure events of the individual. The data regarding seizure events may include data regarding historical and/or current seizure events. For example, the data regarding the seizure events of the individual may include data input over a predetermined period, and/or data input at the event in real-time, using at least one of the said sensors, for example.

The treatment device may be configured to provide biofeedback/tactile stimulation based on a psychophysiological state and behavioural information of the individual. For example, the treatment device may be configured to determine the psychophysiological state and behavioural information of the individual based on the physiological condition of the individual and the data regarding the psychological state and behavioural information of the individual.

The sensor may be provided on a wearable strap US387034. The storage module and the controller may be provided in a wearable device. The sensor may be wirelessly connected to at least one of the storage module and the controller.

The sensor may be configured to determine one or more physiological conditions of the individual that relate to the incidence of a neurological episode. For example, the sensor may be configured to determine at least one of: galvanic skin response (GSR); heart rate; heart rate variability; respiratory rate; temperature; activity level; and one or more electrophysiological properties of an organ of the individual.

The treatment device may comprise one or more electrodes configured to measure galvanic skin response, which is the property of the human body that causes continuous variation in the electrical characteristics of the skin. Changes in the galvanic skin response of an individual may be used to monitor the onset of a neurological episode and emotional disturbance and/or control the biofeedback/tactile stimulation to the individual.

The treatment device may comprise an activity sensor configured to determine and record the activity levels of the individual. For example, the treatment device may be configured to track how active/alert an individual is, or has been, over a predetermined period. Activity/alertness levels may provide an indication of the likelihood of a neurological episode.

The treatment device may comprise a circulatory system sensor configured to determine the blood pressure, heart rate and/or rhythm of the heart of the individual. It may be beneficial for the treatment device to include a circulatory system sensor since a neurological episode can affect the heart rate and/or rhythm of the heart.

The treatment device may comprise a respiratory sensor configured to determine the state of the respiratory system of the individual. It may be beneficial for the treatment device to include a respiratory sensor since a neurological episode can affect the respiratory system, and may even cause respiratory failure.

The data regarding the psychological state and behavioural information of the individual may relate to at least one of: the neuropsychological state; the cognitive psychological state; and the social psychological state; activities in daily life; seizure events of the individual. For example, the treatment device may be configured to collect and/or store data relating to the mood and/or the emotional state of the individual.

The treatment device may be configured to record at least one of the physiological condition and the psychological state and behavioural information of the individual over a predetermined period, for example hours, a day, a week, a month or a year according to the individual's requirement. The treatment device may be configured to determine a change in at least one of the physiological condition and the psychological state and behavioural information of the individual. The treatment device may be configured to provide biofeedback/tactile stimulation to change autonomic function when the change is greater than a predetermined threshold. For example, the treatment device may be configured to provide biofeedback/tactile stimulation to change the individual's autonomic function when mood of the individual changes rapidly, such as if the individual becomes particularly stressed, and/or if the GSR and/or heart rate of the individual increases above a predetermined value.

The controller may be configured to request the individual to input data regarding their psychological state and behavioural information to update the data stored on the storage module. As such, the controller and the storage module may record the psychological activity and behavioural information of the individual over a period of time. Where the individual has access to historical psychological state data and behavioural information, the controller may request the individual to input new psychological state data and behavioural information in order to increase the amount of psychological state data and behavioural information stored on the storage module. Where the individual does not have access to historical psychological state data and behavioural information, the controller may request the individual to input new psychological state data and behavioural information in order to start a record of the psychological state and behavioural information of the individual. The controller may be configured to analyse one or more trends in the psychological state data and behavioural information.

The treatment device may be configured to provide biofeedback/tactile stimulation by virtue of at least one of a haptic, visual and aural signal to the individual. For example, the treatment device may comprise one or more screens configured to display an animation for the purpose of providing biofeedback/tactile stimulation. Additionally or alternatively, the treatment device may comprise a vibrating device, for example a wristband having a vibrating motor, for the purpose of providing biofeedback/tactile stimulation, for example to change the individual's autonomic state.

The treatment device may be a neurological treatment device. The treatment device may be a neuropsychiatric treatment device. The treatment device may be an epilepsy treatment device. The treatment device may be a neurological treatment device. The treatment device may be a stress/anxiety treatment device.

According to another aspect of the present disclosure there is provided a treatment method comprising: determining a physiological condition of an individual using a sensor; storing data regarding the psychological state and behavioural information of the individual on a storage module; and providing biofeedback/tactile stimulation to the individual based on the physiological condition of the individual and the stored data regarding the psychological state and behavioural information of the individual using a controller operatively connected to the sensor and the storage module. The biofeedback/tactile stimulation may be provided to change the autonomic state of the individual. The biofeedback/tactile stimulation may be provided to alleviate epileptic activity. The method may comprise recording the change in at least one of the physiological condition of the individual and the psychological state and behavioural information of the individual over a predetermined period. The method may comprise determining the incidence of a neurological incident, such a seizure, based on the physiological condition of the individual. The method may comprise recording when the individual suffers a neurological episode. The method may comprise analysing, e.g. correlating, the data regarding the psychological state of the individual, the physiological condition of the individual, and/or the incidence of one or more neurological events. The method may comprise adjusting the biofeedback/tactile stimulation in response to the analysis of the data regarding the psychological state and behavioural information of the individual, the physiological condition of the individual, and/or the incidence of one or more neurological events.

The disclosure also provides software, such as a computer program or a computer program product for carrying out any of the methods described herein, and a computer readable medium having stored thereon a program for carrying out any of the methods described herein. A computer program embodying the disclosure may be stored on a computer-readable medium, or it could, for example, be in the form of a signal such as a downloadable data signal provided from an Internet website, or it could be in any other form.

To avoid unnecessary duplication of effort and repetition of text in the specification, certain features are described in relation to only one or several aspects or arrangements of the disclosure. However, it is to be understood that, where it is technically possible, features described in relation to any aspect or arrangement of the disclosure may also be used with any other aspect or arrangement of the disclosure.

DESCRIPTION OF THE DRAWINGS

For a better understanding of the present disclosure, and to show more clearly how it may be carried into effect, reference will now be made, by way of example, to the accompanying drawings, in which:

FIG. 3 shows a neurological and/or neuropsychiatric treatment method;

DETAILED DESCRIPTION OF THE DRAWINGS

Figure 1:
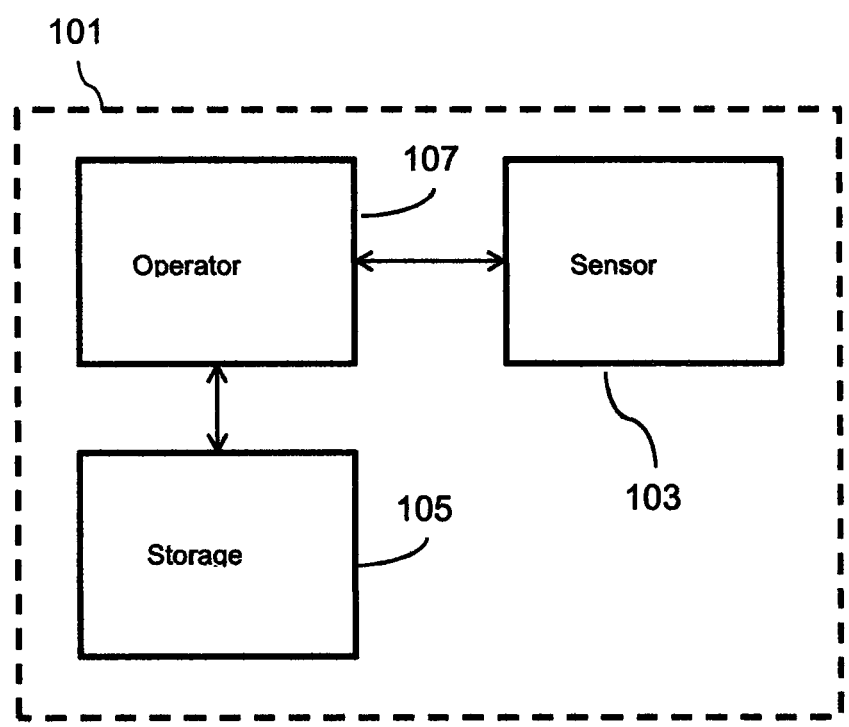
FIG. 1 shows a schematic of a treatment device.

The present disclosure provides a treatment device 101 for the treatment of neurological disorders, such as epilepsy. Whilst the below description makes reference to the treatment of epilepsy, it is understood that the disclosed treatment device 101 and method of treatment 100 may be used to treat any appropriate neuropsychiatric disorder, for example anxiety. Further, the disclosed treatment device 101 and method of treatment 100 provide a way of treating an individual using biofeedback and/or tactile stimulation. Biofeedback is a learned technique that allows an individual to control sympathetic activity, e.g. certain bodily processes that normally happen involuntarily, such as heart rate, blood pressure, muscle tension, and skin temperature, galvanic skin response (GSR).

There have been various attempts to apply biofeedback to the treatment of epilepsy using different physiological parameters (Sterman et al., 1972; Fried et al., 1882; Rockstroh et al., 1992; Nagai et al., 2004). Biofeedback therapy requires that the patient is connected to one or more sensors that can measure one or more physiological signals originating within the body. Biofeedback training in the current invention is specifically directed at the modulation of changes under the control of the autonomic nervous system, achieved through an increase in vigilance or awareness. Autonomic change, reflected in altered levels of galvanic skin response (GSR), is designed to alter neural connectivity of the brain. This method presents an alternative to invasive functional neurosurgical procedures, since the current invention, by modulating peripheral autonomic nervous system non-invasively, also changes activity within the brain. The information acquired from physiological monitoring and psychological and behavioural inputs is used to target producing tailored changes in brain function.

It is known that galvanic skin response, conventionally measured by the resistance between two electrodes applied spaced apart to the skin, varies with the degree of alertness or relaxation of the subject. This phenomenon has been used in the past to assist in training people to relax. WO 93/02622 describes apparatus for assisting relaxation in which a screen display showing a computer-generated animation is viewed by a user whose galvanic skin response is continuously monitored. As the resistance between the electrodes changes, so the animation may be controlled by a suitable programme to give the user a directly perceptible indication of whether they are becoming more relaxed or more tense, for example by seeing whether an animated fish seen against an underwater landscape is swimming to the left or to the right. After some practice, users learn to be able to control the movement seen on screen to be predominantly in the desired direction corresponding to greater relaxation, i.e. they learn to relax. Physiologically, GSR enables biofeedback training of peripheral sympathetic nervous activity, reflecting peripheral autonomic changes.

In particular, it has been found that GSR biofeedback (which is different to relaxation training as has been a standard use of biofeedback) can provide a substantial improvement in the condition of a sufferer of epilepsy can be achieved, particularly in those cases which appear to be resistant to treatment with any of the currently available range of anti-epileptic drugs. One way in which the GSR biofeedback/tactile stimulation acts to reduce epileptic seizures is by affecting cortical potential changes which indicate cortical excitation. However, biofeedback/tactile stimulation may use any appropriate physical condition of the sufferer to provide feedback which the sufferer can use to help control their mental state. For example, the treatment device 101 and method 100 according to the present disclosure may use at least one of the following physical conditions of the sufferer to determine when and/or how to provide appropriate feedback: galvanic skin response; heart rate; respiratory rate; temperature; activity level; and one or more electrophysiological properties of an organ of the individual, for example a muscular contraction and/or a brain signal.

Additionally or alternatively, biofeedback/tactile stimulation may be given to a sufferer based on a psychological state of the individual. For example, the biofeedback/tactile stimulation may be given in response to the mood, emotional state and/or mental condition of the sufferer.

FIG. 1 shows a schematic of a treatment device 101, which comprises a sensor 103 configured to determine a physiological condition of an individual. It will be appreciated that although not shown in the accompanying figures, the treatment device 101 may comprise any appropriate type of sensor that may be used to determine at least one physical state of the individual for the purpose of providing biofeedback/tactile stimulation. For example, the sensor may be an electrodermal activity sensor configured to determine the galvanic skin response of the individual. As mentioned above, the galvanic skin response, for example a change in the galvanic skin response, may be used during biofeedback/tactile stimulation therapy.

The sensor 103 may be integrated into a wearable device, such as a watch or a strap that can be worn around the body. In one or more arrangements, the sensor 103 may be provided on a band that can be attached to an arm, a leg or the upper body of the individual.

The treatment device 101 shown in FIG. 1 further comprises a storage module 105 that is configured to store data regarding the psychological state and behavioural information of the individual and/or incidence of an epileptic event. For example, the storage module 105 may be configured to store data regarding the individual's mood and/or emotional state, and/or data relating to the incidence of a neurological episode.

The treatment device 101 comprises a controller 107 operatively connected to the sensor 103 and the storage module 105, for example by virtue of one or more wired or wireless connections. The controller 107 is configured to receive signals from the sensor 103 and the storage module 105, and provide biofeedback/tactile stimulation to the individual based on the determined physiological condition of the individual and the data regarding the psychological state and behavioural information of the individual. In this manner, the treatment device 101 is able to provide biofeedback and/or send direct stimulation of sympathetic activity to change the individual's autonomic state based on a combination of inputs, such as real-time and/or historical data regarding the physiological condition, psychological state and behavioural information of the individual. The present disclosure is advantageous, therefore, as it allows the psychological state and behavioural information, e.g. mood and/or emotional state, of the individual to be mapped, from which it can be determined when the individual is likely to have a neurological episode. Further, by tracking one or more physiological conditions, such as heart rate and skin conductance, the treatment device 101 is able to more precisely predict the onset of a neurological episode. This is advantageous over known devices which only use data relating to the physiological condition of the individual.

In one arrangement, the treatment device 101 may comprise a sensor 103 attachable to the individual's wrist. For example, the sensor 103 may be integrated into a watch or other wearable device. The controller 107 and the storage module 105 may be provided as part of a smartphone, which is connectable to the wrist sensor by a wireless connection, such as Bluetooth.

Where the treatment device 101 is first used by an individual, a historical profile of the psychological state of the individual may be uploaded to the storage module. For example, the psychological state profile may comprise data on how the individual's neuropsychological state, cognitive psychological state and/or social psychological state varies over time. Further, data regarding historical neurological episodes may be uploaded to the storage module. In this manner, the variation in the individual's psychological state can then be correlated against the incidence of a neurological event, such as a seizure. It can be seen, therefore, that the treatment device 101 may be configured to create a neurological map, i.e. a look-up table, from which it may be determined the psychological state(s) of the individual when a neurological event occurs. Further, the treatment device 101 may be configured to analyse the trend in an individual's psychological state so that one or more psychological state precursors may be established. For example, the psychological state data may show from historical events that an individual is likely to have a neurological episode when they are sad and stressed.

Where there is no historical psychological state data available, the individual's neurological map may be built by the treatment device 101 requesting data relating to the individual's psychological state. For example, the controller 107 may be configured to ask an individual one or more questions relating to their psychological state over a predetermined period. The controller may be configured to run an application that requests psychological state data throughout the course of hours, a day, week, month or year. The application may in addition request data in relation to any neurological episodes that the individual may have suffered so that a correlation may be established between the individual's psychological state and the incidence of a neurological event.

It can be seen, therefore, that the treatment device 101 and method 100 according to the present disclosure is capable of predicting a neurological episode in different ways, for example: 1) by analysing the psychological state of the individual; 2) by analysing the physiological condition of the individual; and/or 3) by analysing data relating to seizure events, which may be historical or current. Importantly, the present disclosure is advantageous over the prior art since it uses a combination of both the psychological state of the individual and the physiological condition of the individual to more accurately determine the likelihood of a neurological event, so that the controller can provide biofeedback/tactile stimulation to prompt the individual to adjust their sympathetic activity.

Figure 2:
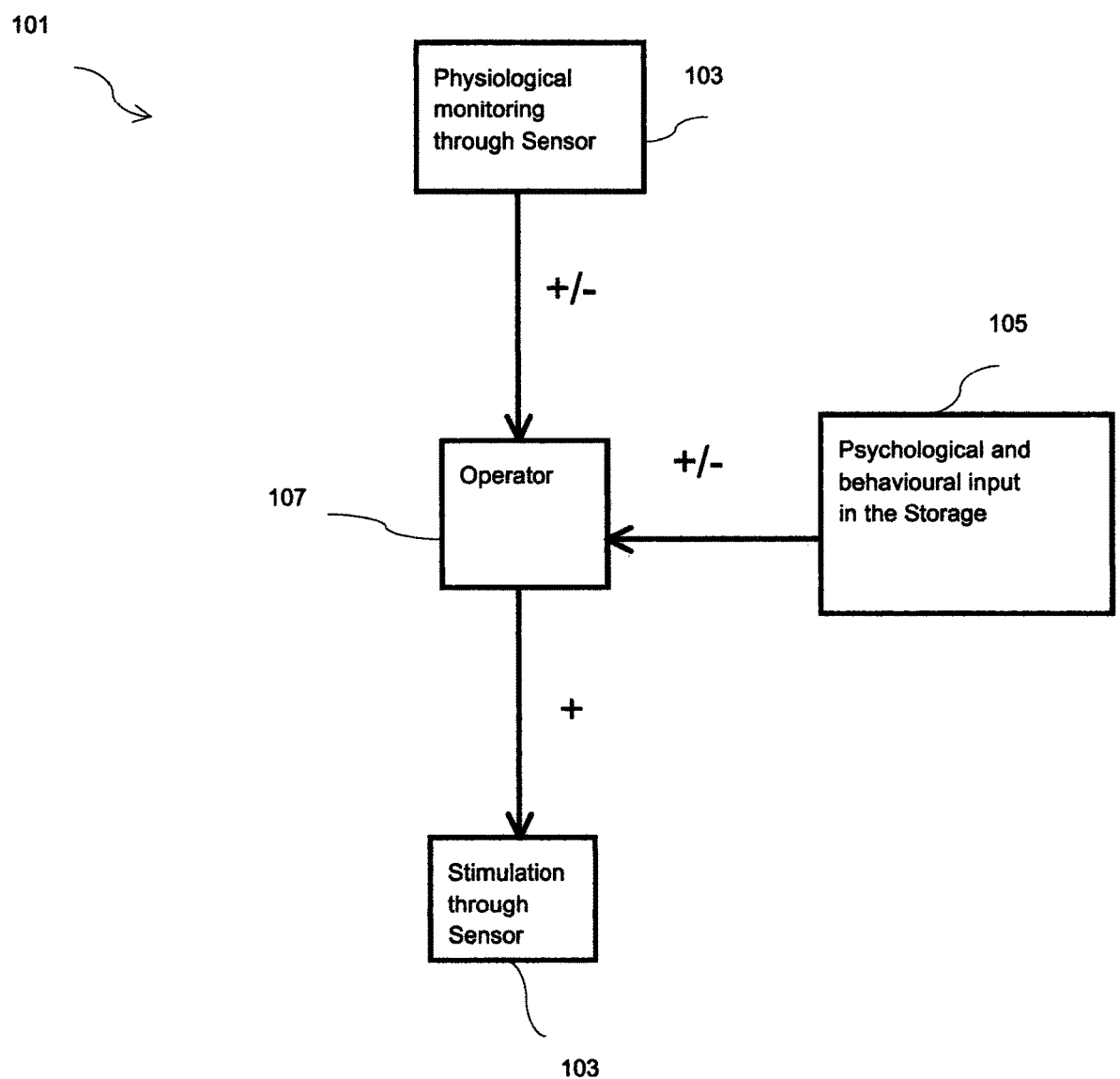
FIG. 2 shows a block diagram describing a flow of device operation

The treatment device 101 may be configured to use psychological state data collected over a period, such as a week or a month, in combination with instantaneous physiological condition data to determine the likelihood of a neurological event. For example, the treatment device 101 may track the mood and/or emotional state of the individual over the course of a few months by requesting periodic updates from the individual. In this manner, when it is determined from the psychological state data that the individual may be particularly susceptible to a neurological event, for example if they are stressed, the treatment device 101 may be configured to provide biofeedback/tactile stimulation when the physiological condition of the individual changes by a predetermined amount. The predetermined amount may be variable, depending on the determined psychological state of the individual. For example, where the individual is stressed, the physiological condition of the individual may need only change by a frequent amount to prompt biofeedback/tactile stimulation, and where the individual is happy and/or calm, the physiological condition of the individual may change by a relatively less amount to prompt biofeedback/tactile stimulation. FIG. 2 shows a block diagram of operation. The treatment device 101 may be configured to provide biofeedback/tactile stimulation in a variety of different ways. For example, the treatment device 101 may be configured to provide biofeedback/tactile stimulation to the individual by virtue of at least one of a haptic, visual and aural signal. The level and/or frequency of the biofeedback/tactile stimulation may depend on the determined likelihood a neurological episode, or indeed the actual occurrence of a neurological episode. For example, where the treatment device 103 determines that there is a low risk of a neurological episode, such as when the individual is calm, but has an elevated GSR, the treatment device 107 may gentle or subtly encourage or remind the individual to increase their sympathetic activity. Conversely, where the treatment device 105 determines that there is a higher risk of a neurological episode, such as when the individual is stressed, and has an elevated GSR and heart rate, for example, the treatment device 107 may more strongly prompt the individual to increase their sympathetic activity.

FIG. 3 shows a flow chart depicting a method of neurological treatment 100. The method comprises a step 110 of storing data regarding the psychological state and behavioural information of the individual on the storage module 105. In one arrangement, the method 100 may comprise uploading historical data regarding the psychological state of the individual. For example, where the individual has a history of a neurological disorder, it is common for the individual to keep a record of their seizure events over a period.

The method 100 may comprise storing data regarding the incidence of a neurological episode of the individual. For example, the individual may store data regarding the time, location and/or type of neurological episode. In other words, the method 100 may comprise constructing on the storage module a record, or diary, of when and/or under what circumstances the individual suffered a neurological episode.

The method may comprise analysing the data regarding the psychological state of the individual and the data regarding the incidence of a neurological episode of the individual. As such, the method 100 may comprise determining a correlation between the individual's psychological state and the incidence of a neurological episode of the individual. In this manner, the method may keep track of the change in the individual's psychological state over a period, for example a week, a month or a year, and use the correlation between the individual's psychological state and the incidence of a neurological episode to determine the likelihood of a neurological episode, for example based on the individual's present psychological state.

The method 100 may comprise a step 120 of determining the physiological condition of an individual using the sensor 103. For example, the method 100 may comprise determining at least one of the galvanic skin response, the heart rate, the respiratory rate, the temperature, the activity level, and one or more electrophysiological properties of an organ of the individual. The physiological condition of the individual may provide a direct indication of the likelihood, or indeed the actual occurrence, of a neurological episode.

The method 100 comprises a step 130 of providing biofeedback/tactile stimulation to the individual based on the physiological condition of the individual and the stored data regarding the psychological state and behavioural information of the individual using the controller 107, which is operatively connected to the sensor 103 and the storage module 105. The controller 107 may be configured to control the operation of one or more biofeedback/tactile stimulation mechanisms, such as an animated display and/or a vibrating device. In one arrangement, the treatment device 101 may comprise a wristband that houses both the sensor 103 and the vibrating device. The method 100 may comprise a step of adjusting the operation, for example the amplitude and/or frequency of the vibrating device in response to a change in the physiological condition of the individual and the stored data regarding the psychological state of the individual.

It can be seen, therefore, that the method of neurological treatment 100 may be implemented in variety of ways, and may be used to treat the neurological disorder in a manner according to the severity of the incidence of the neurological episode. Advantageously, the present disclosure provides a system 101 and method 100 for predicting the onset of a neurological episode and providing biofeedback/tactile stimulation to change autonomic state to alter cortical potential to the individual to prevent a neurological episode. For example, the treatment device 101 may operate in a "prevention mode", in which the treatment device 101 uses data regarding the psychological state of the individual, for example in combination with historical neurological episode incidence data, to predict when it is likely for the individual to suffer another neurological episode. In this manner, where the treatment device 101 determines that the individual is stressed and upset, for example, the treatment device 101 may be configured to provide biofeedback/tactile stimulation using one or more measurements of the physiological condition of the individual to control the manner in which the biofeedback/tactile stimulation is delivered. Thus, the treatment device 101 is capable of delivering a preventative dose of biofeedback/tactile stimulation before the incidence of a neurological episode. It is understood, therefore, the "prevention mode" may function over a relatively long timescale, for example by tracking the psychological state of the individual over the course of a few months and delivering preventative biofeedback/tactile stimulation as the mood and/or emotional state of the individual changes.

Additionally or alternatively, the treatment device 101 may operate in a "precursor mode", in which the treatment device 101 uses data regarding the psychological state and behavioural information of the individual combined with direct measurements of the physiological condition of the individual to identify a precursor, or marker, as to the likelihood of a neurological episode. For example, the treatment device 101 may be configured to track the individual's mood and the GSR of the individual's skin. Thus, the treatment device 101 according to the present disclosure may more accurately predict when a neurological episode is likely to occur. For example, the treatment device 101 may detect a relatively sharp change in one or more physiological conditions of the individual, and compare the said change to data regarding the psychological state of the individual. In this manner, the treatment device 101 is able to more accurately identify the start of a neurological episode and deliver biofeedback/tactile stimulation therapy to reduce the severity of the neurological episode. A further benefit of the treatment device 101 is that false alarms can be prevented through the use of a combined analysis of psychological and physiological data.

It will be appreciated by those skilled in the art that although the disclosure has been described by way of example with reference to one or more arrangements, it is not limited to the disclosed arrangements and that alternative arrangements could be constructed without departing from the scope of the disclosure as defined by the appended claims.

The invention claimed is:

1. A treatment device to treat epilepsy in an individual, the treatment device comprising:
   a storage module that is structured and configured to store data describing a psychological state and behavioral information of the individual;
   a sensor that is structured and configured to measure a physiological galvanic skin response of the individual;
   one or more screens that are structured and configured to display an animation as biofeedback to the individual;
   a vibratory device that is structured and configured to apply a tactile stimulation to the individual; and
   a controller that is configured to, responsive to the data describing the psychological state and behavioral information stored in the storage module and to the physiological galvanic skin response measured by the sensor, cause both (1) the one or more screens to display the animation as biofeedback to the individual and (2) the vibratory device to apply the tactile stimulation to the individual so as to increase sympathetic nerve activity and change the individuals autonomic state and thereby treat epilepsy in the individual.

2. The treatment device of claim 1, wherein the storage module is structured and configured to store data describing one or more of a neuropsychological state, a cognitive psychological state, a social psychological state, activities in daily life, and seizure events of the individual.

3. The treatment device of claim 1, wherein:
   the sensor is structured and configured to measure one or more additional physiological conditions of the individual including heart rate, heart rate variability, respiratory rate temperature, activity level, and electrophysiological properties of an organ.

4. The treatment device of claim 1, wherein the sensor is structured and configured to measure the physiological galvanic skin response of the individual in relation to an activity level of the individual.

5. The treatment device of claim 1, wherein the stored data describes the psychological state and behavioral information of the individual over a predetermined time period.

6. The treatment device of claim 5, wherein the controller is structured and configured to operate the one or more screens to display the animation as biofeedback to the individual and apply the tactile stimulation to the individual when the stored psychological state and behavioral information of the individual and/or the physiological galvanic skin response has changed by greater than a predetermined threshold over the predetermined time period.

7. A method to treat epilepsy in an individual, the method comprising the steps of:
   (a) storing data describing a psychological state and behavioral information of the individual;
   (b) measuring a physiological galvanic skin response of the individual;
   (c) in response to the stored data describing the psychological state and behavioral information of the individual and the measured physiological galvanic skin response of the individual, causing both (1) one or more screens to display an animation as biofeedback to the individual and (2) a vibratory device to apply a tactile stimulation to the individual so as to increase sympathetic nerve activity and change the individuals autonomic state and thereby treat epilepsy in the individual.

8. The method of claim 7, wherein step (a) is performed by storing data describing one or more of a neuropsychological state, a cognitive psychological state, a social psychological state, activities in daily life, and seizure events of the individual.

9. The method of claim 7, wherein step (b) is performed by additionally measuring one or more other physiological conditions of the individual including heart rate, heart rate variability, respiratory rate temperature, activity level, and electrophysiological properties of an organ of the individual.

10. The method of claim 7, wherein step (b) is performed by measuring the physiological galvanic skin response of the individual in relation to an activity level of the individual.

11. The method of claim 7, wherein the stored data describes the psychological state and behavioral information of the individual over a predetermined time period.

12. The method of claim 11, wherein the one or more screens are caused to display the animation as biofeedback to the individual and apply the tactile stimulation to the individual when the stored data describing the psychological state and/or behavioral information of the individual and the measured physiological galvanic skin response of the individual has changed by greater than a predetermined threshold over the predetermined time period.

13. The treatment device of claim 1, wherein the storage module is configured to store data regarding seizure events of the individual, and wherein the controller is configured to provide at least one of the biofeedback and the tactile stimulation based on the data regarding the seizure events of the individual.

14. The treatment device of claim 13, wherein the seizure events include historical and/or current seizure events.

* * * * *